United States Patent [19]

Takahashi et al.

[11] Patent Number: 4,619,938

[45] Date of Patent: Oct. 28, 1986

[54] FATTY ACID DERIVATIVES OF AMINOALKYL NICOTINIC ACID ESTERS AND PLATELET AGGREGATION INHIBITORS

[75] Inventors: Keiko Takahashi; Yasushi Suwabe, both of Tokyo; Toshio Wakabayashi, Tama, all of Japan

[73] Assignee: Terumo Kabushiki Kaisha, Tokyo, Japan

[21] Appl. No.: 713,496

[22] Filed: Mar. 19, 1985

[30] Foreign Application Priority Data

Mar. 21, 1984 [JP] Japan .................................. 59-53796
Feb. 15, 1985 [JP] Japan .................................. 60-26533

[51] Int. Cl.$^4$ .................. A61K 31/455; C07D 213/80
[52] U.S. Cl. ..................................... 514/356; 546/318; 260/404
[58] Field of Search ........................ 546/318; 514/356; 260/404

[56] References Cited

U.S. PATENT DOCUMENTS 2,304,830 12/1942 Katzman .............................. 546/316
4,010,193 3/1977 Harsanyi et al. .................... 546/318

FOREIGN PATENT DOCUMENTS

| 1231702 | 1/1967 | Fed. Rep. of Germany . |
| 1806010 | 5/1970 | Fed. Rep. of Germany . |
| 2129425 | 6/1971 | Fed. Rep. of Germany . |
| 2461798 | 7/1975 | Fed. Rep. of Germany . |
| 2346010 | 10/1977 | France . |
| 2392008 | 12/1978 | France . |
| 464197 | 12/1968 | Switzerland . |
| 1089189 | 11/1967 | United Kingdom . |

OTHER PUBLICATIONS

Chemical Abstract 88:6739m of Japanese Patent 7797974.
Chemical Abstract 100:103136m of Seki, et al.
Chemical Abstracts, vol. 69, No. 5 (1968) 18550 p.
Patent Abstracts of Japan, vol. 5, No. 144, Sep., 11, 1981, p. (C-71) (816).
Patent Abstracts of Japan, vol. 8, No. 168, Aug. 3, 1984, p. (C-236) (1605) #1.
Patent Abstracts of Japan, vol. 8, No. 168, Aug. 3, 1984, p. (C-236) (1605) #2.

*Primary Examiner*—Henry R. Jiles
*Assistant Examiner*—Dale A. Bjorkman
*Attorney, Agent, or Firm*—Burns, Doane, Swecker and Mathis

[57] ABSTRACT

Alkanolamine derivatives and platelet aggregation inhibitors containing the same as an active ingredient are disclosed. The alkanolamine derivatives are novel compounds which possess potent platelet aggregation inhibitory activities and effective in preventing diseases such as thrombosis. As typical compounds are mentioned N-5,8,11,14,17-eicosapentaenoyl-2-aminoethanol, N-nicotinoyl-2-aminoethyl-5,8,11,14,17-eicosapentaenoate, N-ethyl-N-5,8,11,14,17-eicosapentaenoyl-2-aminoethanol, N-butyl-N-5,8,11,14,17-eicosapentaenoyl-2-aminoethanol, N-5,8,11,14,17-3-aminopropylnicotinate, (N-ethyl-N-nicotinoyl-2-aminoethyl)-5,8,11,14,17-eicosapentaenoate and the like.

7 Claims, No Drawings

FATTY ACID DERIVATIVES OF AMINOALKYL NICOTINIC ACID ESTERS AND PLATELET AGGREGATION INHIBITORS

BACKGROUND OF THE INVENTION

1. Field of the Invention

The present invention relates to novel alkanolamine derivatives and platelet aggregation inhibitors containing the same as the active ingredient. Alkanolamines provided by the invention are novel compounds which possess potent platelet aggregation-inhibiting activities. Therefore, they are effective for preventing diseases caused by aggregation of the platelets, that is, such diseases as thrombosis. Also, as it is known that aggregation of the platelets participates in the metastasis of cancers, compounds of the invention are expected to have preventive effects on the cancer metastasis.

2. Description of the Prior Art

α-Linolenic acid which is a trienic higher fatty acid is an essential fatty acid. It is also known that γ-linolenic acid is converted in the living body to dibromo-γ-linolenic acid which is a precursor of prostaglandin $E_1$. In these respects, both of them are important compounds. Among pentaenic higher fatty acids are reported 5,8,11,14,17-eicosapentaenic acid and 7,10,13,16,19-docosapentaenic acid to be contained in fish oils in a large amount and to possess low-density lipoprotein (LDL)-lowering activities. 5,8,11,14,17-Eicosapentaenic acid is known to have an antithrombocytic activity, which is, however, weak so that development of drugs with improved effects has been desired. There is also strong need for antithrombocytic agents which will effectively prevent thrombosis such as myocardial infarction and cerebral thrombosis, one of the major adult diseases.

SUMMARY OF THE INVENTION

As a result of studies on synthesis of alkanolamine derivatives and pharmacological activities thereof, we have found that they have excellent platelet aggregation-inhibitory activities. The present invention has been completed on the basis of the findings.

It is an object of this invention to provide novel alkanolamine derivatives and platelet aggregation inhibitors containing the same as an active ingredient. The alkanolamines of the invention possess potent platelet aggregation inhibitory activities and are useful for preventing diseases caused by aggregation of the platelets such as thrombosis and cancer metastasis.

DETAILED DESCRIPTION OF THE INVENTION

According to the present invention, there are provided alkanolamine derivatives represented by the general formula

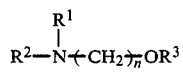  [I]

wherein $R^1$ represents hydrogen atom or a lower alkyl group, $R^2$ represents hydrogen atom or an acyl group derived from nicotinic acid, a trienic higher fatty acid or a pentaenic higher fatty acid, $R^3$ represents hydrogen atom, an acyl group derived from nicotinic acid, a trienic higher fatty acid or a pentaenic higher fatty acid or 3-pyridylmethyl group and n represents 2 or 3 except for cases where both of $R^1$ and $R^2$ represent hydrogen atom.

Further according to the invention, there are provided platelet aggregation inhibitors containing compounds of the above-described general formula [I] as the active ingredient.

$R^1$ in the aforementioned formula [I] means hydrogen atom or lower alkyl groups, preferred examples of which include methyl, ethyl, n-propyl, isopropyl, n-butyl, isobutyl, pentyl and the like. The aforementioned trienic higher fatty acid from which an acyl group in $R^2$ is derived is desirably 9,12,15-octadecatrienic acid (α-linolenic acid), 6,9,12-octadecatrienic acid (γ-linolenic acid) or 8,11,14-eicosatrienic acid (dihomo-γ-linolenic acid). The aforementioned pentaenic higher fatty acid from which an acyl group in $R^3$ is derived is desirably 5,8,11,14,17-eicosapentaenic acid or 7,10,13,16,19-docosapentaenic acid. It is preferred that $R^2$ and $R^3$ are different in the formula [I]. By platelet aggregation inhibitors in the present invention are meant pharmaceutical preparations that possess platelet aggregation-inhibitory activities.

The alkanolamine derivatives of the invention are obtained by condensing nicotinic acid, a trienic higher fatty acid, a pentaenic higher fatty acid or a reactive derivative thereof with corresponding alkanolamine. The reaction temperature is preferably in the range from −10° to 60° C., and the solvent employed is preferably hexane, methylene chloride, chloroform, 1,2-dichlorethane, acetonitrile, benzene, tetrahydrofuran or the like. As the condensing agent used for the condensation is preferably employed, for example, ethyl chloroformate. As the aforementioned reactive derivative may be mentioned thiazolidinethionamide derivatives of the carboxylic acids. The alkanolamine derivatives of the invention are also obtained by a condensation reaction of an alcoholic hydroxyl group following the above-described condensation reaction with nicotinic acid, a trienic higher fatty acid or a pentaenic higher fatty acid. The reaction temperature is preferably in the range from 0° to 90° C., and the reaction solvent used is preferably methylene chloride, chloroform, 1,2-dichloroethane, acetonitrile, dioxane or the like. As the condensing agent used for said condensation reaction are mentioned, for example, N,N′-dicyclohexylcarbodiimide, 2-chloro-1-methylpyridinium p-toluenesulfonate and the like. Alkanolamine derivatives in which both of $R^1$ and $R^2$ are hydrogen atom are prepared by subjecting a phthalimide derivative of an alkanolamine and a carboxylic acid to condensation reaction using N,N′-dicyclohexylcarbodiimide followed by dephthaloylation with hydrazine hydrate. The alkanolamine derivatives in which $R^3$ represents 3-pyridylmethyl group is prepared by reacting an amide derivative obtained from nicotinic acid, a trienic higher fatty acid, a pentaenic higher fatty acid or a reactive derivative thereof and a corresponding alkanolamine with 3-chloromethylpyridine in the presence of a base such as sodium hydride in an aprotonic solvent such as benzene, toluene or the like.

The alkanolamine derivatives of the present invention can be used in platelet aggregation inhibitors as the active ingredient or as one of the active ingredients, which would be effective in any disease caused by aggregation of the platelets and are particularly useful for preventing thrombosis and metastasis of the cancer. Daily doses are in the range between about 100 and 1500 mg in adults, divided in one to three doses as needed. The administration may be by any suitable route, and is desirably by oral route. Intravenous administration is also suitable.

The compounds of the invention are formulated either alone or in administration with carriers or excipients into tablets, powders, capsules or granules. As examples of the carrier or excipient are mentioned calcium carbonate, calcium phosphate, starch, sucrose, lactose, talc, magnesium stearate and the like. The compounds of the invention may also be formulated, in addition to the solid preparations as set forth above, into liquid preparations such as oily suspension and syrup.

The compounds of the invention can be stabilized by inclusion with cyclodextrin.

Examples and Test Examples will be given below to describe the invention in more details, but it is to be understood that the invention is not limited thereby in any way.

EXAMPLE 1

To a solution of 500 mg of 5,8,11,14,17-eicosapentaenic acid thiazolidinethionamide (1.24 mmol) in tetrahydrofuran (10 ml) was added under argon a solution of 84 mg of 2-ethanolamine (1.38 mmol) in tetrahydrofuran (1.5 ml). After reacted at room temperature for 20 min., 10 ml of 1N-aqueous solution of sodium hydroxide was added to the reaction mixture, which was then extracted three times with dichloromethane. Organic layer of the extract was washed with water and dried over anhydrous sodium sulfate. The solvent was removed by distillation under reduced pressure to give 437 mg of the extraction residue. The residue was subjected to silica gel column chromatography and was eluted with 95:5 chloroformmethanol. There was obtained 356 mg (1.03 mmol) of N-5,8,11,14,17-eicosapentaenoyl-2-aminoethanol. Physicochemical properties of the product are given below.

IR $\nu_{max}^{KBr}$ (cm$^{-1}$): 3530, 3340, 1655, 1595, 1530.

$^1$H-NMR (CDCl$_3$) δ: 0.97(3H t, J=7.5 Hz), 1.53–2.33 (8H), 2.67–2.93(8H), 3.39(2H q, J=5 Hz), 3.70 (2H t, J=5 Hz), 5.39(10H bt, J=5.5 Hz).

mass(m/e): 345 (Molecular ion peak), 327 (Dehydration peak), 276.

EXAMPLE 2

To a suspension of 600 mg (4.87 mmol) of nicotinic acid in tetrahydrofuran (15 ml was added 0.68 ml (4.88 mmol) of triethylamine under argon at room temperature, followed by addition of a solution of 556 mg (5.12 mmol) of chloro ethylformate in tetrahydrofuran (1 ml) at −10° C. To the mixture, after reacted at −10° C. for 13 min., was added a solution of 313 mg (5.12 mmol) of 2-aminoethanol in a solvent mixture of tetrahydrofuran (2 ml) and water (2 ml) at 0° C., followed by addition of 0.72 ml (5.17 mmol) of triethylamine. The mixture was reacted at 0° C. for 1 hour and 20 min., followed by addition of 20 ml of water and extraction with three portions of normal butanol. Organic layer of the extract was washed with water and dried over anhydrous sodium sulfate. The solvent removed by distillation under reduced pressure to give 949 mg of residue from the extraction, which was subjected to silica gel chromatography. There was obtained from a fraction eluted with 97:3 chloroformmethanol 608 mg (3.65 mmol) of N-nicotinoyl-2-aminoethanol.

To a solution of 431 mg (1.43 mmol) of 5,8,11,14,17-eicosapentaenic acid in 1,2-dichlorethane (8 ml) were added solutions of 18 mg (0.15 mmol) of 4-dimethylaminopyridine, 324 mg (1.57 mmol) of N,N'-dicyclohexylcarbodiimide and subsequently 237 mg (1.43 mmol) of N-nicotinoyl-2-aminoethanol respectively dissolved in N,N-dimethylformamide (4 ml) under argon at room temperature. The mixture was reacted at room temperature for 20 hours, and precipitates thus formed were separated by filtration and washed with benzene. To the mother liquor was added water, and the mixture was extracted with three portions of dichloromethane. The organic layer of the extract was washed with water and dried over anhydrous sodium sulfate. The solvent was removed by distillation under reduced pressure to give 665 mg of residue from the extraction. The residue was subjected to silica gel column chromatography. There was obtained from fractions eluted with 99:1 chloroform-methanol 418 mg (0.93 mmol) of N-nicotinoyl-2-aminoethyl 5,8,11,14,17-eicosapentaenoate. Physicochemical properties of the product are given below.

IR $\nu_{max}^{neat}$ (cm$^{-1}$): 3305, 1745, 1655, 1595, 1540.

$^1$H-NMR (CDCl$_3$) δ: 0.94 (3H t, J=7.5 Hz), 1.53–2.43 (8H), 2.67–2.93(8H), 3.72(2H q, J=5.5 Hz), 4.30(2H t, J=5.5 Hz), 5.37(10H bt, J=5.5 Hz), 7.37(1H dd, J=8 Hz, 5 Hz), 8.10(1H dt, J=8 Hz, 2 Hz), 8.72(1H dd, J=5 Hz, 2 Hz), 8.99(1H bd, J=2 Hz).

mass(m/e): 450 (Molecular ion peak), 381, 149, 106, 78.

EXAMPLE 3

To a solution of 402 mg (1.44 mmol) of α-linolenic acid in 1,2-dichlorethane (8 ml) were added solutions of 18 mg (0.15 mmol) of 4-dimethylaminopyridine, 328 mg (1.59 mmol) of N,N'-dicyclohexylcarbodiimide and subsequently 240 mg (1.44 mmol) of N-nicotinoyl-2-aminoethanol respectively dissolved in N,N-dimethylformamide (4 ml) under argon at room temperature. The mixture was reacted at room temperature for 14 hours, and precipitates thus formed were separated by filtration and washed with benzene. To the mother liquor was added water, and the mixture was extracted with three portions of dichloromethane. Organic layer of the extract was washed with water and dried over anhydrous sodium sulfate. The solvent was removed by distillation under reduced pressure to give 684 mg of residue from the extraction. The residue was subjected to silica gel column chromatography. There was obtained from a fraction eluted with 99:1 chloroformmethanol 407 mg (0.95 mmol) of N-nicotinoyl-2-aminoethyl 9,12,15-octadecatrienoate. Physicochemical properties of the product are given below.

IR $\nu_{max}^{neat}$ (cm$^{-1}$) 3320, 1750, 1655, 1595, 1545.

$^1$H-NMR (CDCl$_3$) δ:0.97 (3H t, J=7 Hz), 1.13–2.50 (16H), 2.78(2H bt, J=5.5 Hz), 3.73(2H q, J=5.5 Hz), 4.32(2H t, J=5.5 Hz), 5.33(6H bt, J=5.5 Hz), 7.33 (1H dd, J=8 Hz, 5 Hz), 8.10(1H dt, J=8 Hz, 2 Hz), 8.70(1H dd, J=5 Hz, 2 Hz), 8.97(1H bd, J=2 Hz).

mass(m/e: 426 (Molecular ion peak), 357, 149, 106, 78.

EXAMPLE 4

The same procedures as in Example 3 were carried out using 254 mg (0.912 mmol) of γ-linolenic acid to obtain 280 mg of N-nicotinoyl-2-aminoethyl 6,9,12-octadecatrienoate. Physicochemical data of the product are given below.

IR $\nu_{max}^{CHCl_3}$ (cm$^{-1}$) 1740, 1680, 1590, 1520.

mass(m/e): 426 (Molecular ion peak), 149, 106.

EXAMPLE 5

To a solution of 77 mg (0.63 mmol) of nicotinic acid in a mixed solvent of tetrahydrofuran (2 ml) and 1,2-dichlorethane (2 ml) were added under argon at room temperature successively solutions of 7 mg (0.06 mmol) of 4-dimethylaminopyridine, 129 mg (0.63 mmol) of N,N'-dicyclohexylcarbodiimide and 196 mg (0.57 mmol) of N-5,8,11,14,17-eicosapentaenoyl-2-aminoethanol respectively dissolved in 1,2-dichlorethane (1.5 ml). The mixture was reacted overnight at room temperature, and precipitates thus formed were separated by filtration and washed with benzene. To the mother liquor was added water, and the mixture was extracted with three portions of dichloromethane. Organic layer of the extract was washed with water and dried over anhydrous sodium sulfate. The solvent was removed by distillation under reduced pressure to give 311 mg of residue from the extraction. The residue was subjected to silica gel column chromatography. There was obtained from a fraction eluted with 98:2 chloroform-methanol 246 mg (0.55 mmol) of N-5,8,11,14,17-eicosapentaenoyl-2-aminoethyl nicotinate. Physicochemical data of the product are given below.

IR $\nu_{max}^{CHCl_3}$ (cm$^{-1}$): 3425, 1725, 1665, 1580, 1495.

$^1$H-NMR (CDCl$_3$) δ: 0.93(3H t, J=7.5 Hz), 1.50–2.33 (8H), 2.67–2.93(8H), 3.67(2H q, J=5.5 Hz), 4.43(2H t, J=5.5 Hz), 5.36(10H bt, J=5.5 Hz), 7.36(1H dd, J=8 Hz, 5 Hz), 8.28(1H dt, J=8 Hz, 2 Hz), 8.77(1H dd, J=5 Hz, 2 Hz), 9.18(1H bd, J=2 Hz).

mass (m/e): 450 (Molecular ion peak), 381, 106, 78.

EXAMPLE 6

To a solution of 605 mg of 5,8,11,14,17-eicosapentaenic acid in 6 ml of dry chloroform was added 0.25 ml of oxalyl chloride under argon at room temperature. The mixture was reacted for 2 hours. From the reaction mixture were removed the chloroform and the remaining oxalyl chloride by distillation under reduced pressure to give 5,8,11,14,17-eicosapentaenoyl chloride, which was then dissolved in 6 ml of dry chloroform.

Separately, in a solution of 1.78 g of N-ethylethanolamine in 10 ml of dry chloroform was suspended 553 mg of anhydrous potassium carbonate. To the resulting suspension was added the chloroform solution of 5,8,11,14,17-eicosapentaenoyl chloride prepared above dropwise over 15 min., and the mixture was reacted for 2 hours. From the reaction mixture was removed insolubles by filtration, and water was added to the mother liquor. The mixture was extracted once with a mixed solvent of 2:1 chloroform-ether and twice with chloroform. Organic layer of the extract was washed with water and dried over anhydrous sodium sulfate. Then, the solvent was removed by distillation under reduced pressure to give 757 mg of residue from the extraction. The residue was subjected to silica gel column chromatography. There was obtained 662 mg of N-ethyl-N-5,8,11,14,17-eicosapentaenoyl-2-aminoethanol from a fraction eluted with 98:2 chloroform-methanol. Physicochemical data of the product support the structure (III) given below.

IR $\nu_{max}^{neat}$ (cm$^{-1}$): 3400, 1625.

$^1$H-NMR (CDCl$_3$) δ (ppm): 0.97(3H t, J=7.5 Hz), 1.17 (3H t, J=7.5 Hz), 2.60–3.00(8H), 3.17–3.83 (6H), 5.05–5.76(10H).

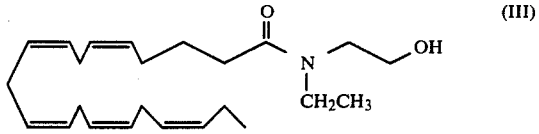

(III)

EXAMPLE 7

To a solution of 1.82 g of 5,8,11,14,17-eicosapentaenic acid in 30 ml of dry chloroform was added 0.80 ml of oxalyl chloride under argon at room temperature. The mixture was reacted for 2 hours. From the reaction mixture was removed the chloroform and the removing oxalyl chloride by distillation under reduced pressure to give 5,8,11,14,17-eicosapentaenoyl chloride, which was then dissolved in 20 ml of dry chloroform.

Separately, in a solution of 7.03 g of N-butylethanolamine in 30 ml of dry chloroform was suspended 1.66 g of anhydrous potassium carbonate. To the suspension was added the chloroform solution of 5,8,11,14,17-eicosapentaenoyl chloride prepared above dropwise over 25 min., followed by reaction for 2 hours. From the reaction mixture were removed insolubles by filtration, and water was added to the mother liquor. The mixture was extracted once with a mixed solvent of 2:1 chloroform-ether and twice with chloroform. Organic layer of the extract was washed with water and dried over anhydrous sodium sulfate. Then, the solvent was removed by distillation under reduced pressure to give 2.52 g of residue from the extraction. The residue was subjected to silica gel column chromatography. There was obtained 2.17 g of N-butyl-N-5,8,11,14,17-eicosapentaenoyl-2-aminoethanol from a fraction eluted with 98:2 chloroform-methanol. Physicochemical data of the product support the structure (IV) given below.

IR $\nu_{max}^{neat}$ (cm$^{-1}$): 3400, 1620.

$^1$H-NMR (CDCl$_3$) δ (ppm): 0.77–1.10(6H), 2.60 –2.93 (8H), 3.17–3.90(6H), 5.10–5.60(10H).

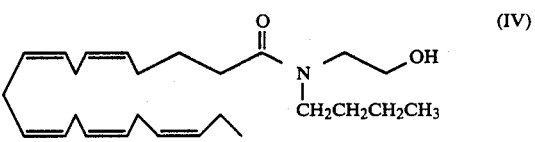

(IV)

EXAMPLE 8

To a solution of 2.40 g of 5,8,11,14,17-eicosapentaenic acid in 15 ml of dry chloroform was added 1.04 ml of oxalyl chloride under argon at room temperature. The mixture was reacted for 2 hours. From the reaction mixture were removed the chloroform and the ramaining oxalyl chloride by distillation under reduced pressure to give 5,8,11,14,17-eicosapentaenoyl chloride, which was then dissolved in 15 ml of dry chloroform.

Separately, in a solution of 5.96 g of N-methylethanolamine in 15 ml of dry chloroform was suspended 2.19 g of anhydrous potassium carbonate. To the suspension was added the chloroform solution of 5,8,11,14,17-eicosapentaenoyl chloride prepared above dropwise over 35 min., followed by reaction for 1 hour 30 min. From the reaction mixture were removed insolubles by filtration, and water was added to the mother liquor. The mixture was extracted once with a mixed solvent of 2:1 chloroform-ether and twice with chloroform. Organic layer of the extract was washed with water and dried over anhydrous sodium sulfate. Then, the solvent was removed by distillation under reduced pressure to give 2.94 g of residue from the extraction. The residue was subjected to silica gel column chromatography. There was obtained 2.16 g of N-methyl-N-5,8,11,14,17-eicosapentaenoyl-2-aminoethanol from a fraction eluted with 98:2 chloroform-methanol. To a solution of 2.10 g of the amide-alcohol product in 20 ml of dry benzene at room temperature were added 1.30 g of nicotinoyl chloride hydrochloride and then 3.23 g of anhydrous potassium carbonate, followed by reaction overnight. From the reaction mixture were removed insolubles by filtration, and water was added to the mother liquor, followed by neutralization with 1N-aqueous solution of lithium hydroxide. The mixture was extracted once with a mixed solvent of 2:1 chloroform-ether and then twice with chloroform. Organic layer of the extract was washed with water and dried over anhydrous sodium sulfate. Then, the solvent was removed by distillation under reduced pressure to give 3.12 g of residue from the extraction. The residue was subjected to silica gel column chromatography. There was obtained 2.05 g of N-methyl-N-5,8,11,14,17-eicosapentaenoyl-2-aminoethylnicotinate from fractions eluted with chloroform to 98:2 chloroformmethanol. Physicochemical data of the product support the structure (V) given below.

IR $\nu_{max}^{CHCl_3}$ (cm$^{-1}$): 1730, 1655, 1595.

$^1$H-NMR (CDCl$_3$) δ (ppm): 0.97(3H t, J=7.5 Hz), 2.63–2.97(8H), 3.75(2H t, J=5.5 Hz), 4.50(2H t, J=5.5 Hz), 5.10–5.60(10H), 7.33(1H dd, J=8 Hz, 5 Hz), 8.23(1H dt, J=8 Hz, 2 Hz), 8.73 (1H dd, J=5 Hz, 2 Hz), 9.17(1H bd, J=2 Hz).

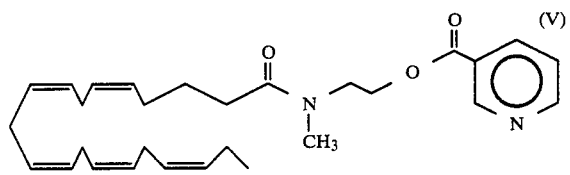
(V)

EXAMPLE 9

To a solution of 834 mg of 9,12,15-octadecatrienoic acid in 8 ml of dry chloroform was added 0.4 ml of oxalyl chloride under argon at room temperature. The mixture was reacted for 2 hours. From the reaction mixture were removed the chloroform and the remaining oxalyl chloride by distillation under reduced pressure to give 9,12,15-octadecatrienoyl chloride, which was then dissolved in 6 ml of dry chloroform.

Separately, in a solution of 2.24 g of N-methylethanol in 4 ml of dry chloroform was suspended 828 mg of anhydrous potassium carbonate. To the suspension was added the chloroform solution of 9,12,15-octadecatrienoyl chloride prepared above dropwise over 10 min., followed by reaction for 1 hour. From the reaction mixture were removed insolubles by filtration, and water was added to the mother liquor. The mixture was extracted once with a mixed solvent of 2:1 chloroform-ether and twice with chloroform. Organic layer of the extract was washed with water and dried over anhydrous sodium sulfate. Then, the solvent was removed by distillation under reduced pressure to give 1.07 g of residue from the extraction. The residue was subjected to silica gel column chromatography. There was obtained 967 mg of N-methyl-N-9,12,15-octadecatrienoyl-2-aminoethanol from a fraction eluted with 98:2 chloroform-methanol. To a solution of 943 mg of the amide-alcohol product in 10 ml of dry benzene were added 626 mg of nicotinoyl chloride hydrochloride and then 1.56 g of anhydrous potassium carbonate, followed by reaction overnight. From the reaction mixture were removed insolubles by filtration, and water was added to the mother liquor, followed by neutralization with 1N-aqueous solution of lithium hydroxide. The mixture was extracted once with a mixed solvent of 2:1 chloroform-ether and twice with chloroform. Organic layer of the extract was washed with water and dried over anhydrous sodium sulfate. Then, the solvent was removed by distillation under reduced pressure to give 1.19 g of residue from the extraction. The residue was subjected to silica gel column chromatography. There was obtained 962 mg of N-methyl-N-9,12,15-octadecatrienoyl-2-aminoethylnicotinate from fractions eluted with chloroform to 98:2 chloroform-methanol. Physicochemical data of the product support the structure (VI) given below.

IR $\nu_{max}^{neat}$ (cm$^{-1}$) 1725, 1650, 1590.

$^1$H-NMR (CDCl$_3$) δ (ppm): 0.97(3H t, J=7 Hz), 2.80 (4H bt, J=5 Hz), 3.57–3.90(2H), 4.46(2H t, J=6 Hz), 5.00–5.70(6H), 7.33(1H dd, J=8 Hz, 5 Hz), 8.23(1H dt, J=8 Hz, 2 Hz), 9.03(1H dd, J=5 Hz, 2 Hz), 9.10(1H bd, J=2 Hz).

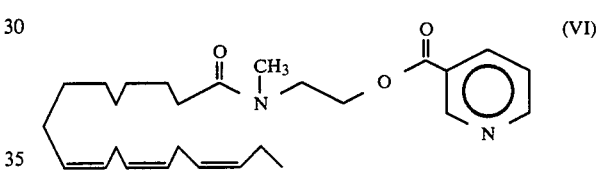
(VI)

EXAMPLE 10

To a solution of 473 mg of N-ethyl-N-5,8,11,14,17-eicosapentaenoyl-2-aminoethanol in 10 ml of dry benzene were added 303 mg of nicotinoyl chloride hydrochloride and then 75 mg of anhydrous potassium carbonate under argon at room temperature. The mixture was reacted overnight. From the reaction mixture were removed insolubles by filtration, and water was added to the mother liquor, followed by neutralization with 1N-aqueous solution of lithium hydroxide. The mixture was extracted once with a mixed solvent of 2:1 chloroform-ether and twice with chloroform. Organic layer of the extract was washed with water and dried over anhydrous sodium sulfate. Then, the solvent was removed by distillation under reduced pressure to give 761 mg of residue from the extraction. The residue was subjected to silica gel column chromatography. There was obtained 510 mg of N-ethyl-N-5,8,11,14,17-eicosapentaenoyl-2-aminoethylnicotinate from fractions eluted with 1:1 benzene-chloroform to chloroform. Physicochemical data of the product support the structure (VII) given below.

IR $_{max}^{neat}$ (cm$^{-1}$): 1730, 1650, 1595.

$^1$H-NMR (CDCl$_3$) δ (ppm): 0.97(3H t, J=7.5 Hz), 1.20 (3H t, J=7.5 Hz), 2.58–2.98(8H), 3.42(2H q, J=7.5 Hz), 3.70(2H t, J=6 Hz), 4.48(2H t, J=6 Hz), 5.05–5.58(10H), 7.33(1H dd, J=8 Hz, 5 Hz), 8.22 (1H dt, J=8 Hz, 2 Hz), 8.72(1H dd, J=5 Hz, 2 Hz), 9.18(1H bd, J=2 Hz).

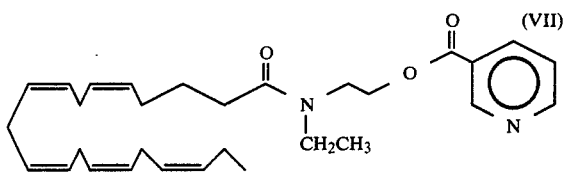

EXAMPLE 11

To a solution of 1.70 g of N-butyl-N-5,8,11,14,17-eicosapentaenoyl-2-aminoethanol in 40 ml of dry benzene under argon at room temperature were added 942 mg of nicotinoyl chloride hydrochloride and then 2.40 g of anhydrous potassium carbonate. The mixture was reacted overnight. From the reaction mixture were removed insolubles by filtration, and water was added to the mother liquor, followed by neutralization with 1N-aqueous solution of lithium hydroxide. The mixture was extracted once with a mixed solvent of 2:1 chloroform-ether and twice with chloroform. Organic layer of the extract was washed with water and dried over anhydrous sodium sulfate. Then, the solvent was removed by distillation under reduced pressure to give 2.14 g of residue from the extraction. The residue was subjected to silica gel column chromatography. There was obtained 2.27 g of N-butyl-N-5,8,11,14,17-eicosapentaenoyl-2-aminoethylnicotinate from fractions eluted with 1:1 benzene-chloroform to chloroform. Physicochemical data of the product support the structure (VIII) given below.

IR $\nu_{max}{}^{neat}$ (cm$^{-1}$): 1725, 1650, 1595.

$^1$H-NMR (CDCl$_3$) δ (ppm): 0.77–1.12(6H), 2.67–2.97 (8H), 3.78(2H t, J=5.5 Hz), 4.57(2H t, J=5.5 Hz), 5.12–5.70(10H), 7.33(1H dd, J=8 Hz, 5 Hz), 8.23(1H dt, J=8 Hz, 2 Hz), 8.73(1H dd, J=5 Hz, 2 Hz), 9.15(1H bd, J=2 Hz).

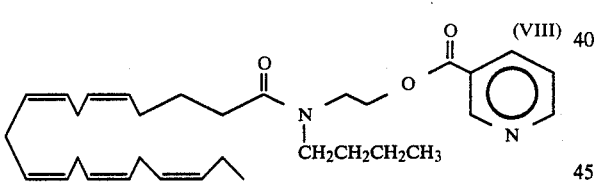

EXAMPLE 12

To a solution of 302 mg of 5,8,11,14,17-eicosapentaenic acid in 3 ml of dry chloroform was added 0.13 ml of oxalyl chloride under argon at room temperature. The mixture was reacted for 2 hours. From the reaction mixture were removed the chloroform and the remaining oxalyl chloride by distillation under reduced pressure to give 5,8,11,14,17-eicosapentaenic acid chloride, which was then dissolved in 5 ml of dry chloroform.

Separately, in a solution of 753 mg of 3-amino-1-propanol in 5 ml of dry chloroform was suspended under argon 276 mg of anhydrous potassium carbonate. To the suspension was dropwise added the chloroform solution of 5,8,11,14,17-eicosapentaenoyl chloride prepared above at room temperature over 10 min. The mixture was reacted for 2 hours. From the reaction mixture were removed insolubles by filtration, and water was added to the mother liquor. The mixture was extracted once with a mixed solvent of 2:1 chloroform-ether and twice with chloroform. Organic layer of the extract was washed with water and dried over anhydrous sodium sulfate. Then, the solvent was removed by distillation under reduced pressure to give 367 mg of residue from the extraction. The residue was subjected to silica gel column chromatography. There was obtained 243 mg of N-5,8,11,14,17-eicosapentaenoyl-3-aminopropanol from a fraction eluted with 98:2 chloroform-methanol. To a solution of the amidealcohol product in 5 ml of dry benzene at room temperature were added 132 mg of nicotinoyl chloride hydrochloride and then 327 mg of anhydrous potassium carbonate. The mixture was reacted overnight. From the reaction mixture were removed insolubles by filtration, and water was added to the mother liquor, followed by neutralization with 1N-aqueous solution of lithium hydroxide. The mixture was extracted once with a mixed solvent of 2:1 chloroform-ether and twice with chloroform. Organic layer of the extract was washed with water and dried over anhydrous sodium sulfate. Then, the solvent was removed by distillation under reduced pressure to give 311 mg of residue from the extraction. The residue was subjected silica gel column chromatography. There was obtained 226 mg of N-5,8,11,14,17-eicosapentaenoyl-3-aminopropylnicotinate from a fraction eluted with 98:2 chloroform-methanol. Physicochemical data of the product support the structure (IX) given below.

IR $\nu_{max}{}^{CHCl_3}$ (cm$^{-1}$): 3450, 1725, 1665, 1595, 1515.

$^1$H-NMR (CDCl$_3$) δ (ppm): 0.97(3H t, J=7.5 Hz), 2.67–2.97 (8H), 3.38(2H q, J=6 Hz), 4.40(2H t, J=6 Hz), 5.10–5.58(10H), 7.28(1H dd, J=8 Hz, 5 Hz), 8.23 (1H dt, J=8 Hz, 2 Hz), 8.70(1H dd, J=5 Hz, 2 Hz), 9.13(1H bd, J=2 Hz).

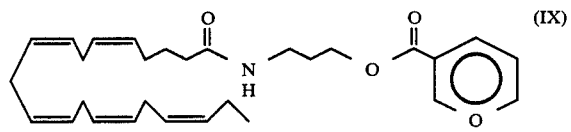

EXAMPLE 13

To a solution of 2.68 g of N-ethylethanolamine in 20 ml of dry chloroform under argon at room temperature were added 3.35 g of anhydrous potassium carbonate and 1.08 g of nicotinoyl chloride hydrochloride successively. The mixture was reacted for 30 min. From the reaction mixture were removed insolubles by filtration, and the mother liquor was concentrated to give 1.72 g of residue. The residue was subjected to alumina column chromatography. There was obtained 989 mg of N-ethyl-N-nicotinoyl-2-aminoethanol from a fraction eluted with chloroform.

Separately, to a solution of 605 mg of 5,8,11,14,17-eicosapentaenic acid in 10 ml of dry chloroform was added 0.26 ml of oxalyl chloride under argon at room temperature. The mixture was reacted for 2 hours. From the reaction mixture were removed the chloroform and the remaining oxalyl chloride to give 5,8,11,14,17-eicosapentaenoyl chloride, which was then dissolved in 6 ml of dry chloroform. The solution thus obtained was added to a solution of 200 mg of N-ethyl-N-nicotinoylethanolamine in 10 ml of dry chloroform under argon at room temperature, followed by reaction overnight. From the reaction mixture were removed insolubles by filtration, and water was added to the mother liquor, followed by neutralization with 1N-aqueous solution of lithium hydroxide. The mixture was extracted once with a mixed solvent of 2:1 chloroform-ether and twice with chloroform. Organic layer of the extract was washed with water and dried over anhydrous sodium sulfate. Then, the solvent was removed by distillation under reduced pressure to give 942 mg of residue from the extraction. The residue was subjected to silica gel column chromatography. There was obtained 621 mg of (N-ethyl-N-nicotinoyl-2-aminoethyl)-5,8,11,14,17-eicosapentaenoate from fractions eluted with chloroform to 98:2 chloroformmethanol. Physicochemical data of the product support the structure (X) given below.

IR $\nu_{max}^{neat}$ (cm$^{-1}$) 1740, 1645, 1595.

$^1$H-NMR (CDCl$_3$) δ (ppm): 0.97(3H t, J=7.5 Hz), 1.17 (3H t, J=6 Hz), 2.61–2.98(8H), 3.42(2H q, J=6 Hz), 3.65(2H t, J=6 Hz), 4.28(2H t, J=6 Hz), 5.08–5.65(10H), 7.27(1H dd, J=8 Hz, 5 Hz), 7.68(1H dt, J=8 Hz, 2 Hz), 8.53–8.72(2H).

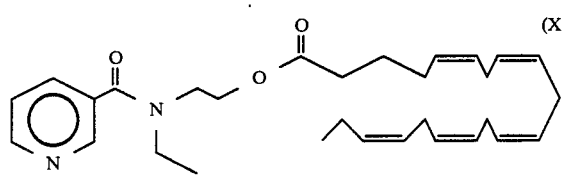

EXAMPLE 14

To a solution of 595 mg of N-methyl-N-5,8,11,14,17-eicosapentaenoyl-2-aminoethanol in 12 ml of dry benzene was added under argon 299 mg of β-picolyl chloride hydrochloride. To the resulting mixture cooled in a water bath to 6° C. was added 147 mg of 60% oily sodium hydride. The mixture was reacted at 6° C. for 2 hours, at room temperature for 16 hours and with heating under reflux for 2 hours. Additional 33 mg of 60% oily sodium hydride was then added, and heating under reflux was continued for additional 30 min. The reaction mixture after allowed to cool was diluted with dichloromethane to double the volume, followed by addition of ice water. The mixture was neutralized under ice cooling with 1N-hydrochloric acid and extracted three times with dichloromethane. Organic layer of the extract was washed with water and dried over anhydrous sodium sulfate. Then, the solvent was removed by distillation under reduced pressure to give 612 mg of residue from the extraction. The residue was subjected to silica gel column chromatography. There was obtained 461 mg of [N-methyl-N-(5,8,11,14,17-eicosapentaenoyl)-2-aminoethyl]-β-picolylether from a fraction eluted with 99:1 chloroform-methanol. Physicochemical data of the product support the structure (XI) given below.

IR $\nu_{max}^{neat}$ (cm$^{-1}$): 1650.

$^1$H-NMR (CDCl$_3$) δ (ppm): 0.97(3H t, J=7.5 Hz) 2.67–3.07(11H), 3.43–3.70(4H), 4.50(2H, s), 5.03–5.60(10H), 7.23(1H dd, J=8 Hz, 5 Hz), 7.60(1H dt, J=8 Hz, 2 Hz), 8.40–8.58(2H).

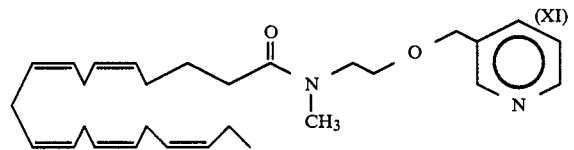

EXAMPLE 15

To a solution of 848 mg of N-butyl-N-5,8,11,14,17-eicosapentaenoyl-2-aminoethanol in 17 ml of dry benzene was added under argon 382 mg of β-picolyl chloride hydrochloride. To the resulting mixture was added at room temperature 228 mg of 60% oily sodium hydride, followed by reaction with heating under reflux for 1 hour 30 min. The reaction mixture after allowed to cool was diluted with dichloromethane to double the volume, followed by addition of ice water. The mixture was neutralized under ice cooling with 1N-hydrochloric acid and then extracted three times with dichloromethane. Organic layer of the extract was washed with water and dried over anhydrous sodium sulfate. Then, the solvent was removed by distillation under reduced pressure to give 883 mg of residue from the extraction. The residue was subjected to silica gel column chromatography. There was obtained 585 mg of [N-butyl-N-(5,8,11,14,17-eicosapentaenoyl)-2-aminoethyl β-picolyl ether from a fraction eluted with chloroform. IR absorption spectrographic data of the product (XII) are given below.

IR $\nu_{max}^{neat}$ (cm$^{-1}$) 1650, 1110.

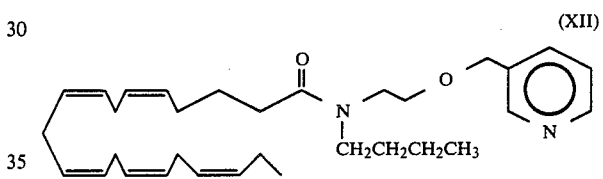

EXAMPLE 16

To a solution of 691 mg of N-5,8,11,14,17-eicosapentaenoyl-2-aminoethanol in 15 mL of dry benzene was added under argon 394 mg of β-picolyl chloride hydrochloride. To the mixture at room temperature was added 264 mg of 60% oily sodium hydride, followed by reaction with heating under reflux for 1 hour 20 min. The reaction mixture after allowed to cool was diluted with dichloromethane to double the volume, followed by addition of ice water. The mixture was neutralized under ice cooling with 1N-hydrochloric acid and then extracted three times with dichloromethane. Organic layer of the extract was washed with water and dried over anhydrous sodium sulfate. Then, the solvent was removed by distillation under reduced pressure to give 982 mg of residue from the extraction. The residue was subjected to silica gel column chromatography. There was obtained 553 mg of (N-5,8,11,14,17-eicosapentaenoyl)-2-aminoethyl β-picolyl ether from a fraction eluted with 99:1 chloroform-methanol. Physicochemical data of the product support the structure (XIII) given below.

IR $\nu_{max}^{CHCl_3}$ (cm$^{-1}$): 3450, 1665, 1515.

$^1$H-NMR (CDCl$_3$) δ (ppm): 0.97(3H t, J=7.5 Hz), 2.60–3.07(8H), 3.37–3.67(4H), 4.50(2H s), 5.03–5.60(10H), 7.23(1H dd, J=8 Hz, 5 Hz), 8.20(1H dt, J=8 Hz, 2 Hz), 8.40–8.58(2H).

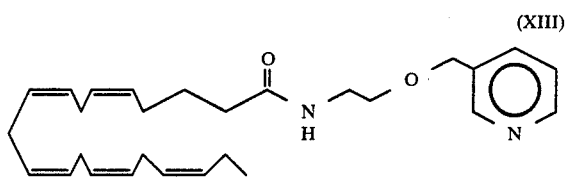

(XIII)

EXAMPLE 17

To a solution of 834 mg of 9,12,15-octadecatrienic acid in 8 ml of dry chloroform was added 0.4 ml of oxalyl chloride under argon at room temperature. The mixture was reacted for 2 hours. From the reaction mixture were removed the chloroform and the remaining oxalyl chloride by distillation under reduced pressure to give 9,12,15-octadecatrienoyl chloride, which was then dissolved in 6 ml of dry chloroform.

Separately, in a solution of 2.25 g of 3-amino-1-propanol in 5 ml of dry chloroform was suspended under argon 830 mg of anhydrous potassium carbonate. To the suspension was added the chloroform solution of 9,12,15-octadecatrienoyl chloride prepared above dropwise at room temperature over 10 min., followed by reaction for 1 hour. From the reaction mixture were removed insolubles by filtration, and water was added to the mother liquor. The mixture was extracted once with a mixed solvent of 2:1 chloroform-ether and twice with chloroform. Organic layer of the extract was washed with water and dried over anhydrous sodium sulfate. Then, the solvent was removed by distillation under reduced pressure to give 1.09 g of residue from the extraction. The residue was subjected to silica gel column chromatography. There was obtained 970 mg of N-9,12,15-octadecatrienoyl-3-amino-1-propanol from a fraction eluted with 98:2 chloroform-methanol. To 576 mg of the amide-alcohol product dissolved in 15 ml of dry benzene was added 340 mg of picolyl chloride hydrochloride. To the mixture was added 227 mg of 60% oily sodium hydride at room temperature. The resulting mixture was reacted with heating under reflux for 1 hour 30 min. The reaction mixture after allowed to cool was diluted with dichloromethane to double the volume, followed by addition of ice water. The mixture was neutralized under ice cooling with 1N-hydrochloric acid and then extracted three times with dichloromethane. Organic layer of the extract was washed with water and dried over anhydrous sodium sulfate. Then, the solvent was removed under reduced pressure to give 903 mg of residue from the extraction. The residue was subjected to silica gel column chromatography. There was obtained 515 mg of (N-9,12,15-octadecatrienoyl)-3-aminopropyl β-picolylether from a fraction eluted with 99:1 chloroformmethanol. IR absorption spectroscopic data of the product (XIV) is given below.

IR $\nu_{max}$ $^{CHCl_3}$ (cm$^{-1}$) 3450, 1665, 1515.

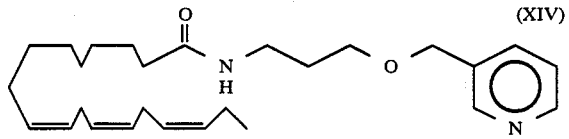

(XIV)

Preparation Example 1: Capsule

| (Formulation) | | |
|---|---|---|
| Active drug: | N—methyl-N—5,8,11,14,17-eicosapentaenoyl-2-aminoethylnicotinate | 200 mg |
| Excipient: | Corn starch | 196.5 mg |
| Lubricant: | Magnesium stearate | 3.5 mg |
| | Total (per capsule) | 400 mg |

To the active drug, N-methyl-N-5,8,11,14,17-eicosapentaenyl-2-aminoethylnicotinate is added the excipient. The mixture, either in powder or in granule, is mixed with the lubricant to a uniform blend, which is filled in hard capsules.

Preparation Example 2: Tablet

| (Formulation) | | |
|---|---|---|
| Active Drug: | N—5,8,11,14,17-eicosapentaenoyl-3-aminopropyl nicotinate | 500 mg |
| Excipient: | Crystalline cellulose | 67 mg |
| Excipient: | Corn starch | 89 mg |
| Excipient: | Lactose | 44 mg |
| Disintegrator: | Calcium carboxymethylcellulose | 25 mg |
| Binder: | Hydroxypropylcellulose | 62.5 mg |
| Lubricant: | Magnesium stearate | 12.5 mg |
| | Total (per tablet) | 800 mg |

The active drug, N-5,8,11,14,17-eicosapentaenoyl-3-aminopropyl nicotinate are meixed with the excipients, the disintegrator and the bonder to a uniform blend. The blend is granulated, and the granules are mixed with the lubricant. The mixture is formed under compression into tablets. As needed, the tablets thus obtained may be coated with an appropriate coating agent (for example, hydroxypropylmethylcellulose or shellac).

Test Example

Platelet Aggregation-Inhibitory Action

Blood was drawn from the carotid artery of a rabbit using a syringe containing 3.8% solution of sodium citrate in an amount of a volumes per volume of the solution. The blood was centrifuged to obtain platelet-rich plasma (PRP: $5 \times 10^5$ platelets/μl).

In a cuvette was placed 250 μl of the PRP, which is warmed in a constant-temperature bath at 37° C. for 2 min. To the warmed cuvette was added 20 μl of a solution of an alkanolamine derivative to be tested (a $7 \times 10^3$M ethanol solution which had been diluted with Trisbuffered isotonic saline solution). The mixture was then incubated for 3 min., followed by addition of a aggregation inducer, an arachidonic acid solution or a collagen solution. Measurement of the platelet aggregation was made by Born's turbidometric method (e.g., described in J. Physiol., Vol. 168, P. 178, 1968). The 50% inhibitory concentration for the platelet aggregation caused by arachidonic acid (100 μM) or collagen (20 μg/ml) is given in Table 1 with reference to Aspirin for comparison.

As shown in Table 1, the typical compounds tested were found to possess marked platelet aggregation inhibitory activities. It was also confirmed that alkanolamine derivatives according to the present invention other than those shown in Table 1 possessed similar anti-aggregation activities. The 50% inhibitory concentration as shown in the table means the concentration of an alkanolamine derivative required for inhibiting aggregation ability of the platelets to 50% when the aggregation ability of the platelets in the absence of the alkanolamine derivative of the invention is taken as 100%.

TABLE 1

Platelet aggregation inhibitory activity

| Structure | Example No. | $R^1$ | $R^2$ or $R^3$ | n | 50% inhibitory concentration (mole) Arachidonic acid | Collagen |
|---|---|---|---|---|---|---|
| $R^2N{-}(CH_2)_n{-}OH$ with $R^1$ on N | 1 | H | (arachidonoyl C(=O)–) | 2 | $2.2 \times 10^{-5}$ | $9.8 \times 10^{-5}$ |
|  | 2 | H | (acyl C(=O)–) | 2 | $1.1 \times 10^{-5}$ | $9.3 \times 10^{-5}$ |
| nicotinoyl-N(R$^1$)(CH$_2$)$_n$–O–R$^3$ | 3 | H | (acyl C(=O)–) | 2 | $4.9 \times 10^{-5}$ | $1.4 \times 10^{-4}$ |
|  | 4 | H | (acyl C(=O)–) | 2 | $3.6 \times 10^{-5}$ | $1.9 \times 10^{-4}$ |
| $R^2N{-}(CH_2)_n{-}O{-}C(=O)$-pyridyl with $R^1$ on N | 5 | H | (acyl C(=O)–) | 2 | $8.8 \times 10^{-6}$ | $9.0 \times 10^{-5}$ |
|  | 6 | Et | (acyl C(=O)–) | 2 | $3.57 \times 10^{-6}$ | $2.73 \times 10^{-4}$ |
| $R^2N{-}(CH_2)_n{-}OH$ with $R^1$ on N | 7 | Bu | (acyl C(=O)–) | 2 | $3.55 \times 10^{-6}$ | $1.87 \times 10^{-4}$ |
|  | 8 |  | (acyl C(=O)–) |  | $6.62 \times 10^{-6}$ | $1.11 \times 10^{-4}$ |
|  | 9 | Me | (acyl C(=O)–) | 2 | $8.24 \times 10^{-6}$ | $2.73 \times 10^{-4}$ |
| $R^2N{-}(CH_2)_n{-}O{-}C(=O)$-pyridyl with $R^1$ on N | 10 | Et | (acyl C(=O)–) | 2 | $4.99 \times 10^{-6}$ | $9.17 \times 10^{-5}$ |
|  | 11 | Bu | (acyl C(=O)–) | 2 | $6.03 \times 10^{-6}$ | $1.97 \times 10^{-4}$ |

TABLE 1-continued

Platelet aggregation inhibitory activity

| Structure | Example No. | $R^1$ | $R^2$ or $R^3$ | n | 50% inhibitory concentration (mole) Arachidonic acid | Collagen |
|---|---|---|---|---|---|---|
| (pyridine-C(=O)-N(R¹)-(CH₂)ₙ-O-R) | 12 | H | (C20:5 acyl) | 3 | $3.44 \times 10^{-6}$ | $5.53 \times 10^{-5}$ |
| 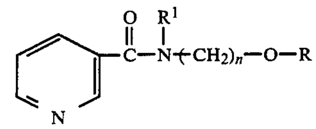 | 13 | Et | (C20:5 acyl) | 2 | $2.55 \times 10^{-4}$ | $4.01 \times 10^{-4}$ |
| | 14 | Me | (C20:5 acyl) | 2 | $5.68 \times 10^{-6}$ | $5.01 \times 10^{-5}$ |
| | 15 | Bu | (C20:5 acyl) | 2 | $7.07 \times 10^{-6}$ | $1.23 \times 10^{-4}$ |
| $R^2-N(R^1)-(CH_2)_n-O-CH_2$-pyridine | 16 | H | (C20:5 acyl) | 2 | $5.68 \times 10^{-6}$ | $5.01 \times 10^{-5}$ |
| | 17 | H | (C18:3 acyl) | 2 | $7.07 \times 10^{-6}$ | $1.23 \times 10^{-4}$ |
| 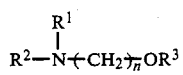 (aspirin) | for comparison | — | — | — | $1.40 \times 10^{-5}$ | $1.36 \times 10^{-5}$ |

Acute Toxicity

Acute toxicity test was conducted by oral administration using ICR male mice (4 weeks old). $LD_{50}$ values are 500 mg/kg bodyweight or high for any of the compounds of the invention, thereby demonstrating high safety.

What is claimed is:

1. Alkanolamine derivative represented by the general formula [I]

$$R^2-N(R^1)-(CH_2)_n-OR^3 \quad [I]$$

wherein $R^1$ represents hydrogen atom or a lower alkyl group, $R^2$ represents an acyl group derived from α-linolenic acid, β-linolenic acid, dihomo-β-linolenic acid, 5,8,11,14,17-eicosapentaenic acid or 7,10,13,16,19-docosapentaenic acid, $R^3$ represents an acyl group derived from nicotinic acid and n represents 2 or 3.

2. Alkanolamine derivative of claim 1 wherein $R^1$ is hydrogen atom or a lower alkyl group, $R^2$ is an acyl group derived from 5,8,11,14,17-eicosapentaenic acid, $R^3$ is an acyl group derived from nicotinic acid and n is 2 or 3.

3. Alkanolamine derivative of claim 2, wherein $R^1$ is hydrogen atom, methyl group, ethyl group or butyl group.

4. Alkanolamine derivative of claim 1 wherein $R^1$ is hydrogen atom or a lower alkyl group, $R^2$ is an acyl group derived from 9,12,15-octadecatrienic acid, $R^3$ is an acyl group derived from nicotinic acid and n is 2 or 3.

5. A platelet aggregation inhibitory pharmaceutical composition comprising an effective platelet aggregation inhibitory amount of an alkanolamine derivative according to claim 1 and a pharmaceutical carrier therefor.

6. A method for preventing disease caused by aggregation of platelets which comprises administering an effective platelet aggregation inhibitory amount of an alkanolamine derivative according to claim 1.

7. A method for preventing thrombosis which comprises adminstering an effective platelet aggregation inhibitory amount of an alkanolamine derivative according to claim 1.

* * * * *